United States Patent [19]
Mehta et al.

[11] Patent Number: 4,790,988
[45] Date of Patent: Dec. 13, 1988

[54] METHOD AND COMPOSITIONS FOR THE TREATMENT OF THROMBOTIC EPISODES

[75] Inventors: Jawahar L. Mehta, Gainesville, Fla.; Tom G. P. Saldeen, Uppsala, Sweden

[73] Assignee: University of Florida, Gainesville, Fla.

[21] Appl. No.: 10,603

[22] Filed: Feb. 4, 1987

[51] Int. Cl.$^4$ .............................................. A61K 37/48
[52] U.S. Cl. ............................... 424/94.64; 424/94.63; 514/17
[58] Field of Search ................... 424/1.1, 94.64, 94.63; 530/324, 330, 329; 514/802, 822, 17

[56] References Cited

U.S. PATENT DOCUMENTS 4,427,646  1/1984  Olexa et al. ...................... 530/300
4,555,290  6/1984  Olexa et al. ...................... 530/324
4,663,146  5/1987  Morser et al. ...................... 424/1.1

OTHER PUBLICATIONS

Thrombosis Research 30; 213–218, 1983, Andersson et al., American Physiological Society, pp. H457–H462, Mehta et al.
Biochimica et Biophysica Acta, 757(1983), pp. 366–370, Gerdin et al.
Prostaglandins Leukotrienes and Medicine 11, pp. 51–61, 1983, Hirose et al.
Prostaglandins Leukotrienes and Medicine 12j, 235–244, 1983, McDonald et al.
Chem. Abstracts, vol. 98, 1983, 193992e.
Chem. Abstracts, vol. 104, 1986, 101747v.
Chem. Abstracts, vol. 104, 1986, 45491t.
Chem. Abstracts, vol. 106, 1987, 38500h.
Biol. Abstracts, 73(6), 1982, 36910.

Primary Examiner—Delbert R. Phillips
Assistant Examiner—T. D. Wessendorf
Attorney, Agent, or Firm—Dennis P. Clarke

[57] ABSTRACT

Fibrinogen degradation product pentapeptide 6A and its variants are used in the treatment of thrombi, in particular myocardial infarcts. In a preferred embodiment pentapeptide 6A and tissue plasminogen activator are administered together to enhance the thrombolytic activity of tissue plasminogen activator.

18 Claims, No Drawings

METHOD AND COMPOSITIONS FOR THE TREATMENT OF THROMBOTIC EPISODES

This is concerned with the treatment of intravenous or intraarterial blood clots in order to institute reperfusion. It is particularly concerned with the use of fibrinogen-degradation product pentapeptide 6A to improve perfusion in cardiac thrombotic episodes.

Thrombotic episodes such as myocardial infarcts, deep vein thrombi, and pulmonary embolisms most commonly are treated with anticoagulation, thrombolytic enzymes and, occasionally in pulmonary embolisms or thrombophlebitis, by surgical removal of the thrombus. The primary objectives of treatment have been to induce acute arterial revascularization, generally by pharmacologic intervention to lyse arterial thrombi and prevent their reformation. Pharmacologic interventions that have been determined to be of benefit in experimental animal models fall into three classes (Wyngaarden et al., "Cecil Textbook of Medicine", Vol. 1: 295, 1985) as shown in the Table below:

Interventions for Limiting Infarct Size

1. Interventions that reduce myocardial oxygen demand and myocardial work.
   a. Beta blockers (for example propranolol
   b. Calcium antagonists (nifedipine, verapamil or diltiazem
   c. Circulatory assistance (intra-aortic balloon counterpulsation)
2. Interventions that increase coronary blood flow to the damaged myocardium.
   a. Nitrates (nitroglycerin)
   b. Calcium antagonists
   c. Hyperosmotic agents (hypertonic mannitol)
   d. Hyaluronidase
   e. Corticosteroids
   f. Circulatory assistance
   g. Thrombolytic agents (tissue plasminogen activator, urokinase, streptokinase)
3. Agents that decrease inflammation, alter immunologic mechanisms, stabilize lysosomal membranes, and/or directly protect myocardial sarcolemmal membranes.
   a. Hyaluronidase
   b. Corticosteroids
   c. Hypertonic agents (hypertonic mannitol)
   d. Glucose, potassium and insulin
   e. Cobra venom
   f. Calcium antagonists
   g. Chlorpromazine
   h. Anti-inflammatory agents (ibuprofen)

Pentapeptide 6A is a fragment of fibrin which is released during proteolytic (plasmin) degradation of fibrin. It has the sequence Ala-Arg-Pro-Ala-Lys, although numerous analogues having qualitatively similar activity are known (B. Gerdin et al., "Biochim. Biphys. Acta (Netherlands)" 757(3): 366–370, 1983). Hereinafter, pentapeptide 6A and all of its functionally equivalent analogues are referred to as "P6A".

P6A has been shown to increase canine coronary blood flow and decrease coronary vascular resistance in a dose-related manner (J. Mehta et al., "Am. J. Physiol." 249(3 pt 2) pH457–462, 1985). The plasma concentrations of 6-ketoprostaglandin F1 alpha, a stable hydrolysis product of prostacyclin, increased in coronary sinus blood samples in conjunction with the increase in coronary blood flow. This study suggested that P6A has potent vasodilator effects on the coronary vascular bed and that these effects are in part mediated by the stimulation of prostacyclin release. P6A also has been shown to increase vasodilation in isolated blood vessels (R. Anderson et al., "Thromb. Res. (U.S.)" 30(3):213–218, 1983).

The importance of prostacyclin in the prevention of thrombosis is disputed. In a study conducted in rabbits, McDonald et al. concluded that PGI2 synthesis may be a relatively unimportant mechanism for prevention of thrombosis ("Prostaglandins Leukotrienes Med.", 12(3): 235–244 [1983]). However, Hirose et al. concluded from a study of the effect of exogenously administered PGI2 methylester on the filtration coefficient of the lung vasculature after microembolis injury that prostacyclin could play an important role in preserving lung cell integrity and preventing increased lung vascular permeability ("Prostaglandins Leukotrienes Med.", 11(1): 51–51 [1983]). Furthermore, various chemically stable prostacyclin analogues are in clinical trials for use as vasodilators and inhibitors of platelet aggregation, and have been observed to inhibit thrombus formation, to counteract the development of occlusive ischemic lesions, and to aid in the decomposition of fresh microemboli ("Drugs of the Future" 11(11):913–921 and 956–958 [1986]).

Tissue plasminogen activator and other less suitable thrombolytic enzymes are currently marketed or in clinical trials. These substances act by activating the apoenzyme plasminogen, which in turn dissolves clots by hydrolyzing fibrin. Only tissue plasminogen activator can be administered by peripheral routes of administration; other plasminogen activating enzymes must be administered by catheter to the site of the thrombus in view of their relative nonspecificity for fibrin and attendant toxicity. In either case the enzyme must reach the thrombus in order to be effective. The arterial or venous occlusion caused by the thrombus impedes blood flow to the thrombus, and this in turn impedes access of the therapeutic enzyme to the thrombus. Methods are needed for maximizing blood flow past the thrombus if at all possible in order to improve therapeutic access.

Accordingly, it is an object of this invention to enhance the efficacy of thrombolytic enzymes.

It is another object of this invention to provide for the in situ release of agents that retard platelet aggregation and that supplement the thrombolytic activity of exogenously administered thrombolytic enzymes.

Other objects of the invention will be apparent from consideration of the following specification as a whole.

SUMMARY OF THE INVENTION

The objects of this invention are accomplished by a method comprising administering to an animal having a thrombus a therapeutically significant amount of P6A. In a preferred embodiment, P6A is administered in the same course of therapy with a direct or indirect acting thrombolytic enzyme.

Therapeutic compositions comprising P6A and such an enzyme are provided for use in the method of this invention.

DETAILED DESCRIPTION OF THE INVENTION

An animal having a thrombus is generally a mammal, preferably a human, in which a fibrin clot is lodged in an artery or a vein. Typically, thrombi in the large arteries or veins are of principal therapeutic concern, although disseminated intravascular clotting or capillary occlusion in particularly sensitive organs such as the lungs and kidneys also are targets of the method herein.

P6A is formulated into therapeutic dosage forms containing conventional pharmaceutical vehicles such as dextrose, sodium chloride, buffers and the like, together with stabilizers such as nonionic surfactants, antioxidants, metal chelating substances, amino acids and other appropriate materials. P6A is available either lyophilized or in aqueous solution.

A therapeutic dosage form is formulated consistent with the intended delivery mode. For example, P6A is preferably delivered intravenously. As a result, it will be desirable to formulate sufficient P6A into the dosage form to delivery a therapeutic dose to the thrombus. The therapeutic dose is an amount sufficient to vasodilate the artery or vein at the site of the thrombus, to inhibit platelet aggregate at the site of the thrombus, and, preferably, to induce the release or activation of endogenous thrombolytic enzymes. The therapeutic dose in dogs at the site of the thrombus is about from 1 to 10 micromoles, preferably about 5 micromoles of the pentapeptide form (Ala-Arg-Pro-Ala-Lys) of P6A. The therapeutic dose in humans or other animals may vary somewhat from this amount, and it will vary depending upon the activity of P6A variants of the pentapeptide species. Suitable dosages also will depend upon the clinical condition of the patient, the nature of the thrombus, and other factors known to the attending physician.

P6A is administered only sufficiently long to result in stable reperfusion. In dog cardiac thrombus models this has been found to be at least about from 10 to in excess of about 20 minutes. The length of the infusion will be shorter where a thrombolytic enzyme such as tissue plasminogen activator is administered with P6A.

Thrombolytic enzymes are defined as being enzymes from any source, including microorganisms, that are capable of dissolving fibrin clots directly, or indirectly by activation of plasminogen, and that are therapeutically acceptable. Therapeutically acceptable means that the enzyme is reasonably specific for fibrin or plasminogen, and that it preferably is not immunogenic in the intended patient. Also included within the scope of the term thrombolytic enzyme are variant enzymes produced by recombinant DNA technology which have amino acid sequences that do not correspond to any enzyme found in nature. Typically, the thrombolytic enzymes will be the products of recombinant cell culture. The preferred thrombolytic enzyme is human tissue plasminogen activator.

The amount of thrombolytic enzyme used in a dosage form comprising such an enzyme generally will be the amount heretofore used in thrombolytic therapy with such enzymes, although it will be understood that an advantage to the use of P6A is that in making the clot more accessible to the thrombolytic enzyme there is promise of being able to use less of the enzyme than has been otherwise conventional. In the case of human tissue plasminogen activator, the dosage at the thrombus has ranged about from 10 to 50 mg of essentially homogeneous recombinant tissue plasminogen activator for the typical 70 kg. patient. Usual intravenous doses are about from 0.25 to 3.00 mg/kg/4–6 hours, with about half of the dose being given as a bolus at the start of therapy.

An example of a composition for use herein will be a sterile lyophilized mixture of about from 20 to 200 micromoles of P6A and about from 20 to 200 mg of tissue plasminogen activator in a buffer containing sufficient amount of a dibasic amino acid for example, arginine to ensure that the tissue plasminogen activator remains soluble and sufficient of an agent such as NaCl (saline) to establish isotonicity. Alternatively, the enzyme and P6A are stored in separate containers for admixture with an aqueous delivery vehicle as needed.

The enzyme and P6A should, but need not, be administered at the same time. However, if administered separately, the enzyme should follow P6A administration by about from 1 to 10 minutes.

Administration generally is intravenous, although it is feasible to administer tissue plasminogen activator intramuscularly together with an adsorption enhancing agent known in the art. Intravenous administration is by injection into a peripheral vein, but delivery by catheter may be preferred for example when using enzymes such as urokinase or when treating deep vein thrombophlebitis. P6A preferably is administered by intravenous infusion into a peripheral vein, as is tissue plasminogen activator.

All literature citations are expressly incorporated by reference.

The following example will illustrate the invention but it is not to be construed as limiting the scope of the invention.

EXAMPLE 1

A thrombus was introduced into the circumflex coronary artery of mongrel dogs by electrical current. Blood flow in the artery was measured by a commercially available electromagnetic flow probe. After stable blood flow for five minutes without electrical current, homogeneous recombinant human tissue plasminogen activator (Genentech) was infused into a peripheral vein for 30 minutes at a dose of 10 microgram/kg/min. In another cohort of animals, pentapeptide 6A was infused intra-arterially proximal to the occlusion at a dose of 5 micromoles/min for 20 min. The tissue plasminogen activator infusion restored coronary blood flow (peak $22\pm12$ ml/min, mean$\pm$SD) in 5 of 7 dogs. The time to flow restoration was $12.3\pm9.1$ minutes and the reflow persisted for $20.0\pm10.9$ minutes. Pentapeptide 6A also restored coronary blood flow (peak $20\pm4$ mel/min) in 7 of 8 animals with zero flow. The mean time to blood flow restoration ($4.3\pm2.9$ minutes) was shorter (P less than 0.05) than with tissue plasminogen activator, but the reflow persisted only for the duration of the infusion ($16.3\pm10.3$ minutes). Pentapeptide 6A administration was associated with a marked increase in plasm 6-keto-PGF 1$\alpha$ in coronary sinus blood samples, thus indicating stimulation of prostacylin release as one mechanism of action of this peptide. Plasma canine tissue plasminogen activator measured by radioimmunoassay of blood samples from the coronary sinus vein of pentapeptide 6A treated animals also was increased over pretreatment dogs.

We claim:

1. A method comprising administering to an animal having a thrombus a composition comprising a therapeutically effective dose of P6A.

2. The method of claim 1 wherein the P6A has the amino acid sequence Ala-Arg-Pro-Ala-Lys.

3. The method of claim 1 wherein the composition additionally contains a thrombolytically effective dose of a thrombolytic enzyme.

4. The method of claim 3 wherein the enzyme is tissue plasminogen activator.

5. The method of claim 1 wherein the thrombus is lodged in a coronary artery.

6. The method of claim 1 wherein the thrombus is a deep vein thrombus.

7. The method of claim 2 wherein the dose is about from 20 to 200 micromoles of P6A at the site of the thrombus.

8. The method of claim 4 wherein the dose of tissue plasminogen activator is about from 0.25 to 3.00 mg/kg.

9. The method of claim 1 wherein a thrombolytically effective dose of a thrombolytic enzyme is also administered to the animal.

10. The method of claim 9 wherein the enzyme is administered to the animal after the P6A.

11. The method of claim 10 wherein the enzyme is tissue plasminogen activator.

12. A sterile composition comprising a thrombolytically effective doses of a thrombolytic enzyme and P6A.

13. The composition of claim 12 wherein the enzyme is tissue plasminogen activator.

14. The composition of claim 12 wherein the P6A has the amino acid sequence Ala-Arg-Pro-Ala-Lys.

15. The composition of claim 14 additionally containing a dibasic free amino acid.

16. The composition of claim 15 wherein the amino acid is arginine.

17. The composition of claim 13 wherein the dose of tissue plasminogen activator is about from 20 to 200 mg.

18. The composition of claim 14 wherein the dose of P6A is about from 20 to 200 micromoles.

* * * * *